(12) United States Patent
Farzin-Nia

(10) Patent No.: US 6,818,076 B1
(45) Date of Patent: Nov. 16, 2004

(54) MULTI-STRAND COIL SPRING

(75) Inventor: Farrokh Farzin-Nia, Inglewood, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 09/533,345

(22) Filed: Mar. 23, 2000

(51) Int. Cl.⁷ .......................... C22K 1/00; C22C 14/00; A61C 7/20
(52) U.S. Cl. .......................... 148/421; 148/669; 433/21
(58) Field of Search .................. 148/669, 421, 148/426, 402; 420/417; 428/37; 433/19, 21, 44.98; 623/1.22

(56) References Cited

U.S. PATENT DOCUMENTS

| | | |
|---|---|---|
| 2,548,864 A | 4/1951 | Brusse |
| 3,052,081 A | 9/1962 | Wallshein ............. 57/139 |
| 3,444,621 A | 5/1969 | Pletcher |
| 3,618,214 A * | 11/1971 | Armstrong |
| 3,772,787 A | 11/1973 | Hanson |
| 3,878,609 A | 4/1975 | Wallshein |
| 4,086,702 A | 5/1978 | Wallshein |
| 4,212,638 A | 7/1980 | Korn |
| 4,248,588 A | 2/1981 | Hanson |
| 4,492,573 A | 1/1985 | Hanson |
| 4,522,590 A | 6/1985 | Pletcher |
| 4,725,229 A | 2/1988 | Miller |
| 4,849,032 A | 7/1989 | Kawaguchi ........... 148/11.5 R |
| 5,018,969 A * | 5/1991 | Andreiko et al. ........ 433/20 |
| 5,080,584 A * | 1/1992 | Karabin |
| 5,344,315 A * | 9/1994 | Hanson |
| 5,356,288 A | 10/1994 | Cohen |
| 5,399,088 A | 3/1995 | Mechley |
| 5,429,501 A | 7/1995 | Farzin-Nia |
| 5,505,616 A * | 4/1996 | Harwell ................ 433/21 |
| 5,540,586 A | 7/1996 | Hanson |
| 5,630,716 A | 5/1997 | Hanson |
| 5,685,711 A | 11/1997 | Hanson |
| 5,711,105 A * | 1/1998 | Schreifels et al. |
| 5,885,074 A | 3/1999 | Hanson |
| 6,042,374 A * | 3/2000 | Farzin-Nia et al. |
| 6,113,390 A * | 9/2000 | Sirney et al. ............. 433/19 |
| 6,241,691 B1 * | 6/2001 | Ferrera et al. ........... 623/1.22 |

FOREIGN PATENT DOCUMENTS

| | | | |
|---|---|---|---|
| DE | 43 07 593 C1 | 8/1994 | ........ D07B/1/06 |
| EP | 0 400 932 A2 | 12/1990 | ........ A61C/7/00 |
| EP | 0 909 665 A1 | 4/1999 | ........ B60C/1/00 |
| GB | 2268518 A * | 1/1994 | ........ A61C/7/20 |
| JP | 58-161746 A * | 9/1983 | ........ C22C/19/03 |
| WO | WO 99/48109 | 9/1999 | ........ H01B/5/00 |
| WO | WO 00/13192 | 3/2000 | ........ H01B/5/00 |

OTHER PUBLICATIONS

Product Brochure, "Nitinol Solutions", Raychem Corporation, Menlo Park, Ca, 1999.*
ASM Handbook, vol. 2: Properties and Selection: Nonferrous Alloys and Special–Purpose Materials, "Shape Memory Alloys", pps. 897–902, 1992.*
Merriam–Webster's Collegiate Dictionary, "coli", pp. 223, 1997.*
"What's In A Twist? Helically Stranded", http://www.occfiber.com/wphelic.html, accessed on Oct. 22, 2002.*
"Nitinol Coil Springs", http://www.ultimatewireforms.com/tech_coil.html, 1998, accessed on Oct. 22, 2002.*

* cited by examiner

Primary Examiner—Roy King
Assistant Examiner—Harry D. Wilkins, III
(74) Attorney, Agent, or Firm—Wood, Herron & Evans, LLP

(57) ABSTRACT

A stranded wire having improved fatigue characteristics and made of a shape memory and/or superelastic material, such as Ni/Ti or alloys thereof. Further, the stranded wire may be coiled along the entire length of the wire or only a portion thereof to form one or more coil springs. The stranded and optionally coiled wire is heat treated to set the wire in the twisted configuration.

17 Claims, 1 Drawing Sheet

MULTI-STRAND COIL SPRING

FIELD OF THE INVENTION

This invention generally relates to stranded wires used in orthodontic, medical and other applications, and more specifically, to coil springs manufactured from stranded wire.

BACKGROUND OF THE INVENTION

Stranding stainless steel wires is known for reducing the stiffness of the stainless steel wires. By stranding is meant that two or more strands of wire are twisted or braided together. The more strands per inch, the lower the stiffness of the stranded wire. Stranding wires is not known for purposes other than stiffness reduction. NiCr wires are likewise stranded to reduce their inherently high stiffness. For a superelastic or shape memory alloy, however, such as a Ni/Ti based alloy, the material inherently has a low stiffness, so the use of stranded wires would not be necessary for stiffness reduction. Ni/Ti wires are becoming increasingly popular for numerous applications, including dental and medical devices. For example, these low stiffness Ni/Ti wires are being used in orthodontic brackets and medical stents.

Coil springs also have many applications in medical and dental industries. For example, in the field of orthodontics, coil springs have replaced elastics "O" rings or soft stainless steel ligature ties in the ligation of arch wires and retainer wires in slots of orthodontic brackets. Also in the field of orthodontics, coil springs are being used in bite fixing appliances to push a patient's lower jaw forward or backward to correct Class 2 and Class 3 malocclusions, i.e., overbites and underbites. Coil springs are also being used in the medical field for stents or devices used in laproscopic surgeries.

Frequently, the coil springs used in oral applications, such as the ligating members or bite fixing coils, will break in the mouth over time due to fatigue. When this happens, the clinicians must remove the appliance and replace it with a new unit, which is very time consuming and costly for the orthodontist. Furthermore, fracture of the coil spring may cause irritation to the patient, as well as prolong the length of treatment due to the appliance ceasing its function after the fracture occurs. Likewise, single strand wires, including Ni/Ti wire, are also subject to premature failure from fatigue. In addition to orthodontic applications, premature failure in single strand and coiled wires due to fatigue is a disadvantage in any application of these wires.

There is thus a need to develop wires having improved fatigue resistance in any environment in which the wires are used.

SUMMARY OF THE INVENTION

The present invention provides a stranded wire having improved fatigue resistance as compared to a single strand of wire. The stranded wire comprises at least two individual strands twisted or braided together, the individual strands being of a shape memory alloy and/or superelastic material. For example, the strands of wire may be made of Ni/Ti or an alloy thereof, preferably comprising at least 50% titanium by weight, and more preferably comprising at least 40% nickel by weight. The stranded wire of the present invention may be a fishing wire, a medical device, a dental device, or any other wire that benefits from improved fatigue resistance in use. In a further embodiment of the present invention, at least a portion of the stranded wire is coiled to form a coil spring. The stranded and coiled wire may be an orthodontic bite fixing device, a stent, a ligature in an orthodontic bracket, an archwire in an orthodontic bracket, or any other coil spring that benefits from improved fatigue resistance in use. The present invention further includes a method of making high fatigue resistant wires, comprising twisting together multiple strands of wire and heat treating the twisted wires to set the shape of the twisted configuration.

These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

Figure 1:
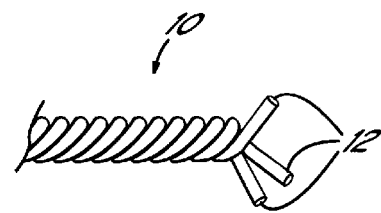
FIG. 1 is a top plan view of a stranded wire of the present invention.

Referring generally to FIG. 1, a stranded wire 10 is shown constructed in accordance with one embodiment of the present invention. A plurality of strands 12, such as the three strands 12 depicted in FIG. 1, are twisted or braided together. The stranded wire 10 comprises at least two strands 12 and up to as many strands 12 as may be practical for the particular application. By way of example and not limitation, about 2 to 7 strands having a diameter of about 0.0005 inch to about 0.007 inch are preferred for a ligating member used with an orthodontic bracket. The fatigue characteristics and stiffness of the stranded wire 10 are in part determined by the pitch of the twisted strands 12. The number of twists per inch generally depends on the size or diameter of the individual strands 12. In general, the greater the number of strands per inch, the lower the stiffness during bending of the stranded wire 10 and the higher the resistance to fatigue over an extended period of use.

The strands 12 of wire comprising the stranded wire 10 are made from shape memory and/or superelastic materials. A shape memory alloy is a metallic material that demonstrates the ability to return to its previously defined shape when subjected to an appropriate heating schedule. Ni/Ti and Ni/Ti-based alloys are the most commercially significant of the shape memory alloys. Ni/Ti materials typically further display superelastic behavior. Advantageously, the Ni/Ti or Ni/Ti alloy comprises at least about 50% Ti by weight. More advantageously, the Ni/Ti or Ni/Ti alloy further comprises at least about 40% Ni by weight. A preferred material for strands 12 is 50Ni-50Ti.

Stranded wire 10 may be used in any application in which increased fatigue resistance is beneficial or desired. One example is fishing wire. A fishing line made from a stranded wire 10 of the present invention will be both flexible and resistant to fracture from fatigue. This increased fatigue resistance will be noticeable as compared to single strand wires made of the same material as the stranded wire 10 of the present invention as well as compared to single strand wires of different metallic materials. The stranded fishing wire is preferably made of Ni/Ti or a Ni/Ti based alloy, as discussed above, and this fishing wire will exhibit increased fatigue resistance and increased flexibility as compared to a stranded wire of a non-shape memory material.

Stranded wire 10 may also find use in the dental field, such as arch wires or retaining wires. It has been known to use Ni/Ti single strand wires in such applications, but the benefit in fatigue resistance by stranding the Ni/Ti wire has never been realized. The stranded wires of the present invention will perform their function in the oral environment for longer than a non-stranded wire, thus decreasing the frequency of replacement and avoiding prolonged treatment time from non-functioning of the device pending replacement.

Stranded wire 10 may also find use in the medical field. Ni/Ti wires are biocompatible, making them desirable for biomedical uses. Adding the stranding feature of the present invention, there is provided a device that is compatible in the human body and that exhibits increased resistance to fatigue-induced fractures. By way of example, stranded wires 10 may be inserted into the body through a tube, such as in the case of guide wires.

Figure 2:
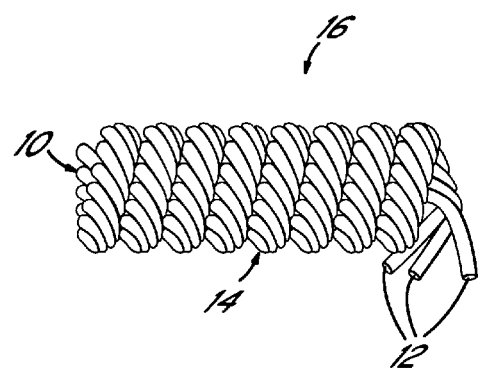
FIG. 2 is a top plan view of a stranded and coiled wire of the present invention.
Figure 3:
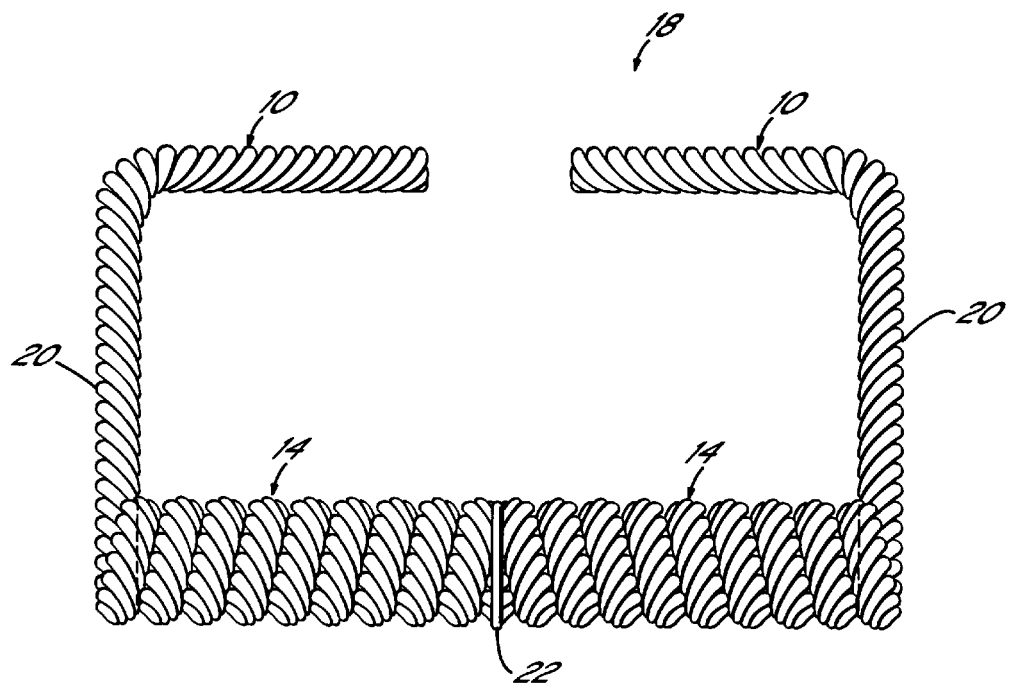
FIG. 3 is a top plan view of a stranded and coiled ligating member for an orthodontic bracket.

In a further embodiment of the present invention, the stranded wire 10 may be coiled along all or part of the length of the wire to create one or more coil springs 14, as depicted generally in FIGS. 2 and 3. Coil springs manufactured from single strand wire also experience fracture from fatigue, but a stranded and coiled wire 16 of the present invention will exhibit improved fatigue resistance, thus allowing its use for a longer period of time than a single strand coil spring. The coil spring, however, may experience a decrease in force as a result of the stranding, and thus, a balance is to be achieved between flexibility, fatigue resistance and strength for a given application. As in the stranded wire 10 of FIG. 1, the strands 12 may be made of a shape memory and/or superelastic material, such as Ni/Ti or a Ni/Ti-based alloy.

In FIG. 2, the three-strand wire 10 is coiled along substantially its entire length. By way of example and not limitation, this stranded and coiled wire 16 may be used as a coil extension spring in an orthodontic bite fixing appliance, such as that described and depicted in commonly owned, copending application Ser. No. 09/307,403 entitled "Orthodontic Bite Fixing Appliance", expressly incorporated by reference herein in its entirety. By way of further example, the stranded and coiled wire 16 may be used as a medical stent or an orthodontic arch wire or retaining wire.

FIG. 3 depicts a ligating member 18 for a self-ligating bracket as disclosed in commonly owned co-pending U.S. patent application Ser. No. 09/533,125, entitled "Self Ligating Orthodontic Bracket", filed on even date herewith in the names of Farrokh Farzin-Nia and Rohit C. L. Sachdeva, expressly incorporated herein by reference in its entirety. In the specific embodiment of FIG. 3, a coil spring segment 14 is formed in one portion of the stranded wire 10, and a straight leg portion 20 of stranded wire 10 remains for engaging the body of an orthodontic bracket, such as within bores formed in the sides of the bracket body. The ligating member 18 of FIG. 3 has two stranded wires 10 each having a coil spring segment 14, the coil spring segments 14 being wound in opposite directions and attached to each other at an intermediate point 22 in the ligating member 18. Various embodiments of a ligating member comprising stranded wire and one or more coil spring segments is fully described in co-filed application Ser. No. 09/533,125.

It may be appreciated that several examples of applications for the stranded and optionally coiled wire of the present invention have been described, but are in no way exhaustive of the potential applications for this invention. In any environment in which a single strand wire or single strand coiled wire is used that is subjected to conditions in which fracture by fatigue is a possibility, the stranded and optionally coiled wire of the present invention is applicable. Moreover, when the stranded and optionally coiled wire of the present invention is made of a shape memory and/or superelastic material, such as Ni/Ti or a Ni/Ti-based alloy, both high flexibility and high fatigue resistance may be achieved.

In manufacturing a stranded or stranded and coiled wire of the present invention, two or more strands of wire are twisted together, and this twisted wire is subjected to a heat treatment to set the shape of the twisted configuration. This heat treatment prevents the stranded wire from unraveling. The heat treatment temperature and time are dependent upon the particular material and diameter of the individual strands 12, but generally, for Ni/Ti and Ni/Ti-based alloys, heat treating is performed for between about 1 second and about 15 minutes at a temperature of about 300° C. to about 550° C.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A stranded orthodontic wire having a coil spring, the wire comprising at least two individual strands of wire twisted together, each strand in the wire twisted relative to another strand such that each strand is nonlinear, and each strand in the wire made of a material selected from the group consisting of shape memory alloys, superelastic materials, and combinations thereof, and said twisted strands further coiled along at least a portion of the stranded wire to form the coil spring.

2. The stranded wire of claim 1, wherein said strands of wire are made of Ni/Ti or alloys thereof.

3. The stranded wire of claim 2, wherein said strands of wire comprise at least 50% Ti by weight.

4. The stranded wire of claim 3, wherein said strands of wire comprise at least 40% Ni by weight.

5. The stranded wire of claim 1, wherein said wire is heat treated after twisting the strands together to set its shape.

6. The stranded wire of claim 5, wherein said wire is heat treated for about 1 to about 15 seconds at a temperature of about 300° C. to about 550° C.

7. The stranded wire of claim 1, wherein said stranded orthodontic wire is an orthodontic bite fixing device.

8. The stranded wire of claim 1, wherein said stranded orthodontic wire is a ligature in an orthodontic bracket.

9. The stranded wire of claim 1, wherein said stranded orthodontic wire is an archwire in an orthodontic bracket.

10. A stranded orthodontic wire having a coil spring, the wire comprising at least two individual strands of wire wherein each strand in the stranded wire is made of a material selected from the group consisting of shape memory alloys, superelastic materials, and combinations thereof, and wherein each strand in the stranded wire is stranded relative to another strand along the length of said strands such that each strand is nonlinear, and wherein the stranded wire is further coiled along at least a portion of the length of said strands to form a coil spring.

11. The wire of claim 10, wherein said stranded wire is coiled along the entire length of said strands.

12. The wire of claim 10 wherein the at least two individual strands of wire are twisted along the length of said strands, said twisted strands being further coiled along at least a portion of the length of said strands.

13. The wire of claim 10, wherein the at least two individual strands of wire are braided along the length of said strands, said braided strands being further coiled along at least a portion of the length of said strands.

14. A method of making a stranded orthodontic wire having a coil spring, the method comprising the steps of:

twisting together a plurality of strands of wire, wherein each strand in the stranded wire is twisted relative to another strand such that each strand is nonlinear;

heat treating said twisted wire strands at a temperature of about 300° C. to about 550° C. for a time sufficient to set the shape of the twisted configuration; and coiling the twisted wire strands to form a coil spring.

15. The method of claim 14, wherein said twisted wire is heat treated for about 1 second to about 15 minutes.

16. The method of claim 14, wherein said strands of wire are made of a material selected from the group consisting of shape memory alloys, superelastic materials, and combinations thereof.

17. The method of claim 16, wherein said strands of wire are made of Ni/Ti or alloys thereof.

* * * * *

UNITED STATES PATENT AND TRADEMARK OFFICE
CERTIFICATE OF CORRECTION

PATENT NO.   : 6,818,076 B1
DATED        : November 16, 2004
INVENTOR(S)  : Farrokh Farzin-Nia It is certified that error appears in the above-identified patent and that said Letters Patent is hereby corrected as shown below:

<u>Title page,</u>
Item [56], References Cited, OTHER PUBLICATIONS, "Merriam-Webster's Collegiate Dictionary" reference, "coli" should be -- coil --.

<u>Column 1,</u>
Line 29, "elastics" should be -- elastic --.

Signed and Sealed this

Fifth Day of April, 2005

JON W. DUDAS
*Director of the United States Patent and Trademark Office*